United States Patent
Turbett et al.

(10) Patent No.: US 12,269,525 B2
(45) Date of Patent: Apr. 8, 2025

(54) METHOD AND APPARATUS FOR LOADING

(71) Applicant: Turbett Surgical, Inc., Rochester, NY (US)

(72) Inventors: Robert E. Turbett, Penfield, NY (US); Richard D. Richmond, Canandaigua, NY (US)

(73) Assignee: Turbett Surgical, Inc., Henrietta, NY (US)

( * ) Notice: Subject to any disclaimer, the term of this patent is extended or adjusted under 35 U.S.C. 154(b) by 0 days.

(21) Appl. No.: 16/396,029

(22) Filed: Apr. 26, 2019

(65) Prior Publication Data
US 2019/0263434 A1   Aug. 29, 2019

Related U.S. Application Data

(63) Continuation of application No. 14/741,837, filed on Jun. 17, 2015, now Pat. No. 10,272,936.
(Continued)

(51) Int. Cl.
*B62B 3/00* (2006.01)
*A47B 81/00* (2006.01)
(Continued)

(52) U.S. Cl.
CPC .............. *B62B 3/002* (2013.01); *A47B 81/00* (2013.01); *A61L 2/07* (2013.01); *B01L 1/50* (2013.01);
(Continued)

(58) Field of Classification Search
CPC ........... B62B 3/002; B62B 3/04; B65G 67/20; B60B 33/00; A47B 81/00; B01L 9/02;
(Continued)

(56) References Cited

U.S. PATENT DOCUMENTS 2,981,196 A    4/1961   Zimmermann et al.
3,275,393 A *  9/1966   Conklin ................ A47J 39/006
                                                    219/214
(Continued)

FOREIGN PATENT DOCUMENTS

AU    2006200911 B2    3/2007
CA       2759434 A1   11/2010
(Continued)

OTHER PUBLICATIONS

European Patent Office (EPO), European Search Report for corresponding EP Appl. No. 15743752.6-1370, dated Nov. 24, 2017.
(Continued)

*Primary Examiner* — Regina M Yoo
(74) *Attorney, Agent, or Firm* — Jodi A. Reynolds, Esq.; Harter Secrest & Emery LLP (57) ABSTRACT

Presented is a method and apparatus for loading. The method includes loading one of an individually sterilized item or a non-sterile item into the cart, the cart comprising a top portion, and a plurality of wheels fixedly coupled to a bottom portion of the cart able to freely rotate and support the cart. The method further includes loading a sterilizing cabinet onto the cart, the sterilizing cabinet being removeably affixed to the cart and comprising an interior, the interior containing collectively sterilized items, the interior being sterilizable and resealable.

13 Claims, 4 Drawing Sheets

Related U.S. Application Data (60) Provisional application No. 62/031,222, filed on Jul. 31, 2014.

(51) Int. Cl.

| | | |
|---|---|---|
| *A61L 2/07* | (2006.01) | |
| *B01L 1/00* | (2006.01) | |
| *B01L 9/02* | (2006.01) | |
| *B60B 33/00* | (2006.01) | |
| *B62B 3/04* | (2006.01) | |
| *B65G 67/20* | (2006.01) | |
| *B08B 3/00* | (2006.01) | |
| *C12M 1/00* | (2006.01) | |
| *C12M 1/12* | (2006.01) | |

(52) U.S. Cl.
CPC ............... *B01L 9/02* (2013.01); *B60B 33/00* (2013.01); *B62B 3/04* (2013.01); *B65G 67/20* (2013.01); *B08B 3/00* (2013.01); *C12M 23/52* (2013.01); *C12M 37/00* (2013.01)

(58) Field of Classification Search
CPC . B01L 1/50; A61L 2/07; C12M 37/00; C12M 23/52; B08B 3/00
See application file for complete search history.

(56) References Cited

U.S. PATENT DOCUMENTS

| | | | |
|---|---|---|---|
| 3,347,619 A | 10/1967 | Vischer | |
| 3,351,422 A | 11/1967 | Jones et al. | |
| 3,853,329 A * | 12/1974 | McDonald | A61B 50/10 280/47.35 |
| 3,905,662 A | 9/1975 | Richmond | |
| 3,925,043 A | 12/1975 | Matrone et al. | |
| 4,052,589 A * | 10/1977 | Wyatt | A47B 31/02 219/386 |
| 4,399,667 A * | 8/1983 | Lamb | F25D 3/125 312/236 |
| 4,643,303 A | 2/1987 | Arp et al. | |
| 4,661,326 A | 4/1987 | Schainholz | |
| 4,670,227 A * | 6/1987 | Smith | A61L 11/00 422/297 |
| 4,671,943 A | 6/1987 | Wahlquist | |
| 4,728,504 A | 3/1988 | Nichols | |
| 4,997,240 A | 3/1991 | Schmalzi et al. | |
| 5,072,960 A | 12/1991 | Sperko | |
| 5,205,627 A | 4/1993 | Davison et al. | |
| 5,224,812 A | 7/1993 | Oslin et al. | |
| 5,324,489 A | 6/1994 | Nichols et al. | |
| 5,346,075 A | 9/1994 | Nichols et al. | |
| 5,352,416 A | 10/1994 | Wagner | |
| 5,369,892 A | 12/1994 | Dhaemers | |
| 5,372,787 A | 12/1994 | Ritter | |
| 5,417,729 A | 5/1995 | Greenleaf, Sr. | |
| 5,553,986 A | 9/1996 | Napierkowski et al. | |
| 5,732,821 A | 3/1998 | Stone et al. | |
| 5,843,388 A | 12/1998 | Arroyo et al. | |
| 5,893,618 A | 4/1999 | LePage, Jr. et al. | |
| 5,968,459 A | 10/1999 | Nalepa et al. | |
| 6,196,303 B1 | 3/2001 | Hepper | |
| 6,572,819 B1 | 6/2003 | Wu et al. | |
| 6,620,390 B1 | 9/2003 | Wagner | |
| 6,789,815 B2 | 9/2004 | Moss et al. | |
| 6,867,393 B1 * | 3/2005 | Lewis | A61L 11/00 219/401 |
| 7,455,067 B1 * | 11/2008 | Cotton | A47L 15/0092 134/72 |
| 7,950,679 B2 * | 5/2011 | Claffy | A47J 39/006 280/47.35 |
| 8,454,901 B1 | 6/2013 | Snyder, III | |
| 8,505,959 B2 | 8/2013 | Darling, III | |
| 9,126,613 B2 * | 9/2015 | Savage | B62B 3/004 |
| 9,439,992 B2 | 9/2016 | Webb et al. | |
| 9,616,143 B2 * | 4/2017 | Snyder | A61L 2/07 |
| 2002/0064478 A1 | 5/2002 | Davis | |
| 2004/0001783 A1 | 1/2004 | Bowen | |
| 2004/0011689 A1 | 1/2004 | Bauer | |
| 2004/0062693 A1 | 4/2004 | Lin et al. | |
| 2004/0090028 A1 | 5/2004 | Trogstam | |
| 2004/0178137 A1 | 9/2004 | Itoh et al. | |
| 2004/0256270 A1 | 12/2004 | Gleichauf et al. | |
| 2005/0000553 A1 | 1/2005 | Noguchi et al. | |
| 2005/0238530 A1 | 10/2005 | Frieze et al. | |
| 2006/0124486 A1 * | 6/2006 | Faust, III | A61B 50/31 206/363 |
| 2006/0260515 A1 * | 11/2006 | Hodges | A61B 50/13 108/6 |
| 2007/0039294 A1 | 2/2007 | Airey | |
| 2008/0087231 A1 | 4/2008 | Gabriel | |
| 2008/0104990 A1 | 5/2008 | Lee et al. | |
| 2008/0149001 A1 * | 6/2008 | Hodges | A61B 50/15 108/6 |
| 2009/0223972 A1 | 9/2009 | Allen | |
| 2009/0272859 A1 | 11/2009 | Pippin | |
| 2010/0154353 A1 | 6/2010 | Cesa et al. | |
| 2010/0166603 A1 | 7/2010 | Opie | |
| 2011/0108554 A1 | 5/2011 | Ladison et al. | |
| 2011/0114522 A1 | 5/2011 | Alston et al. | |
| 2011/0291372 A1 * | 12/2011 | Stryker | B62B 3/005 280/47.35 |
| 2011/0308210 A1 | 12/2011 | Crabtree et al. | |
| 2012/0082589 A1 | 4/2012 | Ladison et al. | |
| 2012/0174922 A1 | 7/2012 | Virr et al. | |
| 2013/0313029 A1 | 11/2013 | Franco | |
| 2013/0322004 A1 | 12/2013 | Park | |
| 2014/0079589 A1 * | 3/2014 | Landgrebe | A61L 2/20 96/417 |
| 2014/0348722 A1 | 11/2014 | Gray-Dreizler et al. | |
| 2015/0023839 A1 * | 1/2015 | Snyder | A61L 2/07 422/28 |
| 2015/0107627 A1 | 4/2015 | Snyder et al. | |
| 2015/0231012 A1 | 8/2015 | Rapoport | |
| 2015/0284018 A1 * | 10/2015 | Krosney | B62B 5/0026 422/292 |
| 2015/0314026 A1 | 11/2015 | Mauzerall et al. | |
| 2016/0008503 A1 | 1/2016 | Webb et al. | |
| 2016/0346415 A1 | 12/2016 | Webb et al. | |

FOREIGN PATENT DOCUMENTS

| | | | |
|---|---|---|---|
| CA | 2960460 | | 3/2014 |
| CN | 1455684 A | | 11/2003 |
| CN | 1799632 A | | 7/2006 |
| CN | 201200633 Y | | 3/2009 |
| DE | 202004002095 U1 | | 4/2004 |
| DE | 202008001263 U1 | | 7/2008 |
| EP | 0077831 B1 | | 9/1986 |
| EP | 1905343 A1 | | 4/2008 |
| EP | 2737870 A2 | | 6/2014 |
| FR | 2986147 A1 | | 8/2013 |
| GB | 272284 | | 6/1927 |
| JP | S63-146647 | | 9/1988 |
| JP | H10-211262 | | 8/1998 |
| JP | H11-276559 | | 10/1999 |
| JP | 2001520552 | | 10/2001 |
| JP | 2002502668 | | 1/2002 |
| JP | 2007061596 | | 3/2007 |
| JP | 4189453 B2 | | 12/2008 |
| JP | 2010-246847 | | 11/2010 |
| KR | 20110059395 A * | 6/2011 | ............. A61L 9/14 |
| KR | 20120064349 A * | 6/2012 | ............. A61L 2/20 |
| WO | 9847545 A3 | | 10/1998 |
| WO | 9940948 A1 | | 8/1999 |
| WO | 2007000639 A1 | | 1/2007 |
| WO | 2007045943 A1 | | 4/2007 |
| WO | 2008061137 A2 | | 5/2008 |
| WO | 2010128408 A4 | | 11/2010 |
| WO | 2012106506 A2 | | 8/2012 |
| WO | 2014159696 A1 | | 10/2014 |

(56) References Cited

FOREIGN PATENT DOCUMENTS

OTHER PUBLICATIONS

European Patent Office (EPO), European Search Report for corresponding EP Appl. No. 15827680.8-1101, dated Jan. 31, 2018.
International Search Report and Written Opinion of the International Searching Authority in corresponding International Application No. PCT/US2015/010464; mailed Apr. 3, 2015.
International Search Report and Written Opinion of the International Searching Authority in corresponding International Application No. PCT/US2016/025262; mailed Jul. 5, 2016.
Steris, "AMSCO Loading Car and Transfer Carriage—Type III", Steris Corporation, pp. 1-2, Jul. 10, 1998, <www.steris.com>.
Steris, "Loading Equipment for AMSCO Evolution and Evolution—L Steam Sterilizers—North America", Steris Corporation, pp. 1-4, Feb. 1, 2011, <www.steris.com>.
Steris, "AMSCO Sterilization Container System, Users Guide", Steris Corporation, pp. 1-10, Apr. 2006, <www.steris.com>.
European Patent Office (EPO), Communication from EP Appl. No. 15743752.6 dated Sep. 29, 2016.
European Patent Office (EPO), Communication from EP Appl. No. 16774196.6 dated Nov. 17, 2017.
Japanese Patent Office (JPO), Office Action from JP Patent Appl. No. 2016-567331 dated Aug. 22, 2017.
Australia Govt., IP Australia, Office Action from AU Patent Appl. No. 2015211408 dated Jan. 12, 2017.
Canadian Intellectual Property Office (CIPO), Office Action from CA Patent Application No. 2,938,346 dated Apr. 18, 2017.
Aesculap Surgical Technologies SterilContainer System, archived on Jan. 24, 2013, accessed at http://web.archive.org/web/20130124053037/http://www.aesculapusa.com/assets/base/doc/DOC132RevD-SterilContainerSystem.pdf.
European Patent Office (EPO), Extended European Search Report from EP Appl. No. 16774196.6 dated Aug. 24, 2018.
Chinese Patent Office (CPO), Office Action from CN Patent Application No. 201580015570.0 dated Jun. 5, 2019.
Japanese Patent Office (JPO), Office Action from JP Patent Application No. 2017-550718 dated Mar. 27, 2019.
Thempson, "Sterile Container System & Baskets", Thempson Surgical Instruments, pp. 1-48. Accessed at http://www.thempson.com/downloads.html.
Canadian Intellectual Property Office (CIPO), Office Action from corresponding Canadian Patent Application No. 2,956,904 dated Jan. 30, 2018.
IP Australia, Paper No. 2, Notice of Acceptance from corresponding AU Patent Application No. 2015296977 dated Sep. 6, 2018.
IP Australia, Examination Report No. 1 from corresponding AU Patent Application No. 2015296977 dated Sep. 4, 2017.
IP Australia, Examination Report No. 2 from corresponding AU Patent Application No. 2015296977 dated Aug. 3, 2018.
Canadian Intellectual Property Office (CIPO), Office Action from corresponding Canadian Patent Application No. 2,956,904 dated Oct. 25, 2018.
International Search Report and Written Opinion of the International Searching Authority in corresponding International Application No. PCT/US2015/036159; mailed Sep. 14, 2015.
European Patent Office, Extended European Search Report in corresponding EP Application No. 19210878.5, dated Apr. 8, 2020.
European Patent Office, Office Action in corresponding EP Application No. 16774196.6, dated Feb. 6, 2020.

\* cited by examiner

METHOD AND APPARATUS FOR LOADING

FIELD OF THE INVENTION

Exemplary embodiments of the present disclosure relate to a method and apparatus for loading and more particularly to a method and apparatus for loading and maintaining sterilized items. Exemplary embodiments of the present disclosure even more particularly relate to transporting and presenting collectively and individually sterilized items to a surgical field.

BACKGROUND OF THE INVENTION

Sterilization is a term referring to any process that eliminates (removes) or kills microbial life, including transmissible agents (such as fungi, bacteria, viruses, or spore forms) present on a surface, contained in a fluid, in medication, or in a compound such as biological culture media. Sterilization can be achieved by applying heat, chemicals, irradiation, high pressure, and filtration or combinations thereof.

In general, surgical instruments and medications that enter an already aseptic part of the body (such as the bloodstream, or penetrating the skin) must be sterilized to a high sterility assurance level. Examples of such instruments include scalpels, hypodermic needles and implantable medical devices (IMD), such as artificial pacemakers. This also includes all of the outer garments worn by the medical personnel, drapes used on or over the patient, and drapes used to divide the sterile portion of an operating room and the non-sterile portion of the operating room.

One method of sterilization involves passing a sterilizing agent, such as steam through a cabinet. For effective sterilization, steam needs to penetrate the cabinet load uniformly. Accordingly, the cabinet must not be overcrowded, and the lids of the bottles and containers must be left ajar. During the initial heating of the chamber, residual air must be removed. Indicators should be placed in the most difficult places for the steam to reach to ensure that steam actually penetrates there.

A filter is typically placed over the vent to keep particles or extraneous materials from entering the cabinet before, during or after the sterilizing process. Once the sterilizing process is completed the filter needs to be removed and inspected by medical professionals to verify the integrity of the sterilizing process was maintained. If it is discovered during the inspection that the filter did not remain intact, the sterilization process has to be repeated with a new filter.

BRIEF SUMMARY OF THE INVENTION

In view of the foregoing, it is an object of the present invention to provide a method and apparatus for loading maintaining, transporting and presenting collectively sterilized, non-sterile and individually sterilized items.

A first exemplary embodiment of the present invention provides a method of loading a cart. The method includes loading one of an individually sterilized item or a non-sterile item into the cart, the cart comprising a top portion, and a plurality of wheels fixedly coupled to a bottom portion of the cart able to freely rotate and support the cart. The method further includes loading a sterilizing cabinet onto the cart, the sterilizing cabinet being removeably affixed to the cart and comprising an interior, the interior containing collectively sterilized items, the interior being sterilizable and resealable.

A second exemplary embodiment of the present invention provides an apparatus for loading. The apparatus includes a cart, the cart configured to contain one of individually sterilized items or non-sterile items and comprising a top portion, and a plurality of wheels fixedly coupled to a bottom portion of the cart able to freely rotate and support the cart. The apparatus further includes a sterilizing cabinet, the sterilizing cabinet being removeably affixed to the cart and comprising an interior, the interior configured to contain collectively sterilized items, the interior being sterilizable and resealable.

A third exemplary embodiment of the present invention provides an apparatus for loading. The apparatus includes a cart, the cart having one of a plurality of individually sterilized items or a plurality of non-sterile items and comprising a top portion, and a plurality of wheels fixedly coupled to a bottom portion of the cart able to freely rotate and support the cart. The apparatus further includes a sterilizing cabinet, the sterilizing cabinet being removeably affixed to the cart and comprising an interior, the interior configured to contain a plurality of collectively sterilized items in the interior, the interior being sterilizable and resealable.

The following will describe embodiments of the present invention, but it should be appreciated that the present invention is not limited to the described embodiments and various modifications of the invention are possible without departing from the basic principle. The scope of the present invention is therefore to be determined solely by the appended claims.

DETAILED DESCRIPTION OF THE INVENTION

Prior to any surgical procedure, all of the items that will be used during the procedure should be properly sterilized. This includes all of the medical instruments, such as scalpels and needles as well as the outer garments worn by the medical professionals. Typically, each of the fabric items, such as garments and drapes, that are used during a medical procedure are individually sterilized and then wrapped in a sealed bag prior to the medical procedure. This allows the medical professionals to open and unwrap only the items that will be needed for a given procedure while maintaining the sterility of the unused items.

The individually sterilized items are typically kept in a cart, which is more commonly known as a case cart. The purpose of the case cart is twofold. First, the case cart maintains the individually sterilized items in a manner that will sufficiently ensure that the packaging and thus the sterile nature of each of the individually sterilized items is maintained. Second, the case cart provides accessibility and mobility for its contents, which can be wheeled from one area to another with relative ease.

Figure 1:
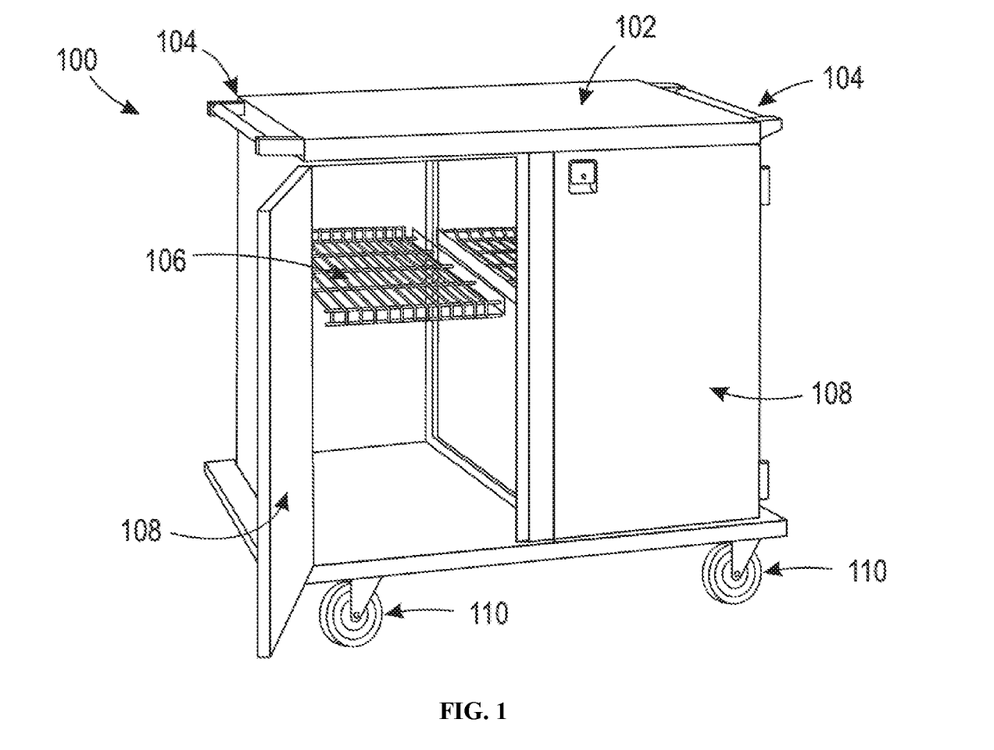
FIG. 1 is a perspective view of a case cart suitable for use in practicing exemplary embodiments of this disclosure.

Shown in FIG. 1 is an exemplary case cart 100. Case cart 100 includes a substantially flat top 102, push handles 104, shelf 106, doors 108, and wheels 110. Case cart 100 can be constructed out of any durable material that is strong enough to maintain its shape and form under significant weight and also able to be sterilized. Ideally, case cart 100 is constructed out of a steel or aluminum alloy or a combination thereof. It should be understood that case cart 100 is merely an exemplary embodiment of a case cart. Alternative exemplary embodiments of case cart 100 do not include an enclosed interior section, but offers an open midsection with one or multiple shelves.

Flat top 102 of case cart 100 provides a flat surface to maintain other items. Exemplary embodiments of the present disclosure provide that flat top 102 is rigid enough to maintain the weight of a sterilizing cabinet or other like sterilizing device or apparatus. Flat top 102 may also include a locking mechanism (not shown). The locking mechanism provides a means to removeably affix a sterilizing cabinet to case cart 100 on flat top 102. Exemplary embodiments of the locking mechanism include any means that would allow a sterilizing cabinet to be securely affixed to case cart 100 on flat top 102 such that a sterilizing cabinet only moves when case cart 100 moves. Exemplary embodiments of the locking mechanism include clamps, laches, slots, bolts, screws, and the like.

Push handles 104 of case cart 100 provide the means for a user to more easily push and pull case cart 100. In the embodiment shown in FIG. 1, push handles 104 are provided on opposite sides of case cart 100. Each of the push handles 104 span the width of case cart 100. It should be appreciated, that embodiments of push handles 104 include push handles 104 being located on all sides or only on one side of case cart 100 along with different configurations.

Case cart 100 also includes shelf or shelves 106. FIG. 1 depicts case cart 100 with only one shelf 106, however, exemplary embodiments of case cart 100 can include both numerous shelves 106 and zero shelves 106. Shelves 106 provide a stable location for maintaining individually sterilized items or non-sterile items. Exemplary embodiments of individually sterilized items include sterile garments, dividers or drapes that are typically used during a procedure or in an operating room. The individually sterilized items are each individually sterilized and then wrapped in a sealed wrapping that maintains the sterility of the item by preventing extraneous materials from coming into direct contact with the individually sterilized items. Non-sterile items include any type of instrument, tool, garment, apparatus, device, or thing that has not been sterilized as well as those that have not been sterilized and can be, will be or is typically used in or in conjunction with a procedure or in an operating room. Non-sterile surgical tape or gauze are non-limiting exemplary embodiments of non-sterile items.

In one exemplary embodiment, shelf or shelves 106 are flat and rigid enough to maintain the weight of a sterilizing cabinet or other like sterilizing device or apparatus. Shelf or shelves 106 may also include a locking mechanism (not shown). The locking mechanism provides a means to removeably affix a sterilizing cabinet to shelf or shelves 106. Exemplary embodiments of the locking mechanism include any means that would allow a sterilizing cabinet to be securely affixed to shelf or shelves 106 such that a sterilizing cabinet only moves when case cart 100 moves, for the case that shelf or shelves 106 are affixed to the body of case cart 100. For the case the shelf or shelves 106 are removable from case cart 100, the locking mechanism includes any means that allow a sterilizing cabinet to be securely affixed to shelf or shelves 106 such that the sterilizing cabinet only moves when shelf or shelves 106 move. Exemplary embodiments of the locking mechanism include clamps, laches, slots, bolts, screws, and the like. In a further exemplary embodiment, the sterilizing cabinet can be directly and removeably affixed to case cart 100 rather than on shelf or shelves 106, such as on the bottom or sides of case cart 100.

Also shown in FIG. 1 are door or doors 108. Door or doors 108 are able to open and close for access to the interior of case cart 100, which is typically in the midsection of case cart 100. Door or doors 108 are physically connected to case cart 100. Door or doors 108 can be attached through the use of a hinge or hinges which allows the doors to swing open. Door or doors 108 can also include a latch or lock for securely keeping door or doors 108 from opening when not desired. It should be appreciated that exemplary embodiments of door or doors 108 include any mechanism that allows for door or doors 108 to move from an open position to a closed position to provide access to the interior of case cart 100. Exemplary embodiments of case cart 100 provide that the interior of case cart 100 is of the shape and size such that an entire sterilizing cabinet can reside within the interior of case cart 100 and door or doors 108 are free to open and close without being obstructed should a sterilizing cabinet reside within the interior of case cart 100.

FIG. 1 also includes wheels 110 on case cart 100. Exemplary embodiments of wheels 110 provide a means for case cart 100 to be moved from one location to another. Embodiments of wheels 110 are configured to hold a significant amount of weight and are still able to freely rotate such that when a user pushes or pulls case cart 100, wheels 110 rotate in a direction of the user's actions. Embodiments of wheels 110 include the ability for wheels 110 to be selectively placed into a locked position wherein movement of wheels 110 is prohibited. Exemplary embodiments of case cart 100 include the four wheels 110 located at each corner of the bottom of case cart 100. However, it should be appreciated that alternative embodiments of case cart 100 include more or less than four wheels as well as different arrangements.

Figure 2:
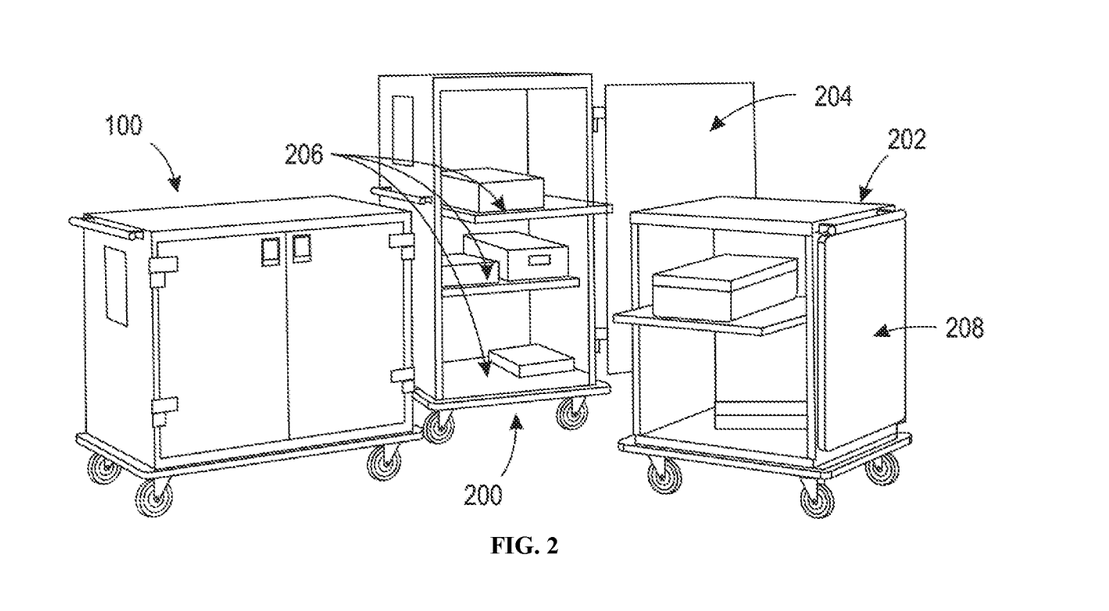
FIG. 2 depicts numerous case carts suitable for use in practicing exemplary embodiments of this disclosure.

Exemplary embodiments of case cart 100 include numerous shapes and sizes. FIG. 2 depicts three such case carts. Shown in FIG. 2 is case cart 100, case cart 200, and case cart 202. As illustrated in FIG. 2, case cart 200 has almost all of the characteristics of case cart 100 except that it appears taller and includes a single door 204 and multiple shelves 206. Case cart 202 also has almost all of the characteristics of case cart 100 except that it too only includes a single door 208. It should be appreciated that case cart 100, case cart 200, and case cart 202 though they may appear differently, each of their elements (i.e., doors, wheels, shelves, and flat top portion) are configured to functionally perform the similar task of providing mobility and the ability to maintain individually sterilized items.

Figure 3:
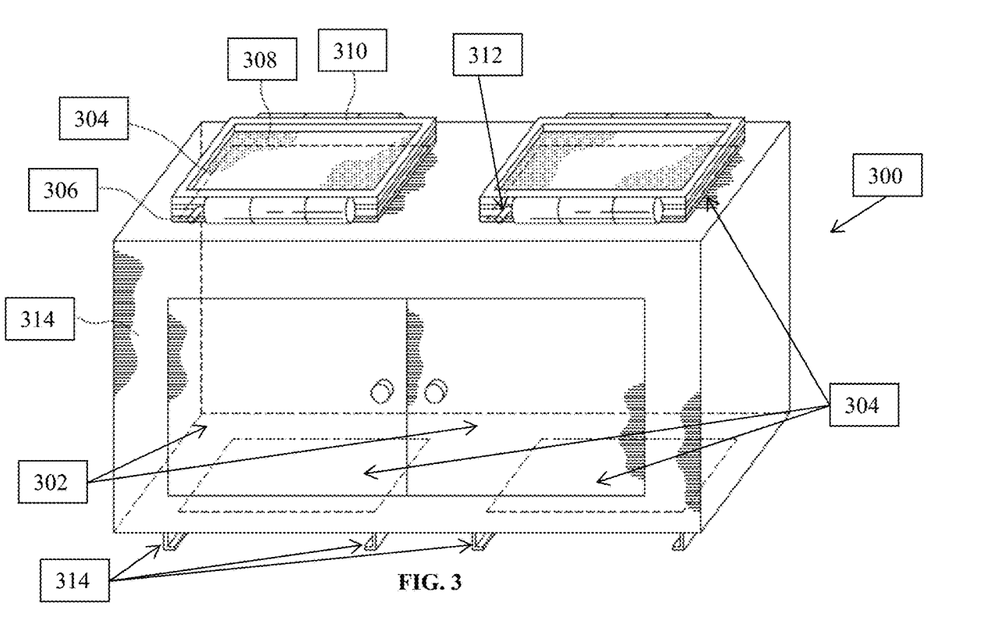
FIG. 3 is a perspective view of a sterilizing cabinet suitable for use in practicing exemplary embodiments of this disclosure.

FIG. 3 depicts a perspective view of a cabinet or sterilizing cabinet 300. Exemplary embodiments of sterilizing cabinet 300 are able to collectively sterilize items that are placed within its interior. Exemplary embodiments of a sterilizing cabinet include any type of cabinet with the ability to be repeatedly subjected to a sterilizing process. Exemplary embodiments of a sterilizing cabinet further include the ability to use a filter or filters for passing a sterilizing agent into and out of the sterilizing cabinet. Shown in FIG. 3 is sterilizing cabinet 300 with door or doors 302, vents 304, primary filters 306, secondary filters 308, filter holders 310, and filter lock 312. Door or doors 302 are able to open and close for access to the interior of sterilizing cabinet 300. Door or doors 302 are physically connected to sterilizing cabinet frame 314. Door or doors 302 can be attached through the use of a hinge or hinges which allows the doors to swing open. Alternatively, door or doors 302 can be removable from sterilizing cabinet 300 through the use of clamps (not shown). It should be appreciated that exemplary embodiments of door or doors 302 include any mechanism that allows for door or doors 302 to move from an open position to a closed position to provide access to the interior of sterilizing cabinet 300. It should be appreciated that sterilizing cabinet 300 as depicted in FIG. 3 includes two doors 302, however, alternative exemplary embodiments of sterilizing cabinet 300 include as few as one door 302 as well as numerous doors 302.

Sterilizing cabinet 300 in the embodiment illustrated in FIG. 3 includes four vents 304. Exemplary embodiments of sterilizing cabinet 300 provide that sterilizing cabinet 300 may include one or more vents 304. As depicted in FIG. 3, sterilizing cabinet 300 includes two vents 304 on the top of sterilizing cabinet 300 and two vents 304 on the bottom of sterilizing cabinet 300. Vents 304 provide numerous small openings for the passage of a sterilizing agent, such as sterilizing steam. The small openings in vents 304 can be holes or slits. In an alternative embodiment, vents 304 are fenestrated.

Primary filter 306 in conjunction with filter holder 310 covers vent 304. Primary filter 306 with filter holder 310 forms a sealed interface with the adjacent portions of sterilizing cabinet 300 such that during the operation of a sterilizing cycle, any sterilizing steam that passes through the vents 304 must also pass through primary filter 306. Exemplary embodiments of primary filter 306 provide that primary filter 306 can be made of any porous material that (1) allows for the passage of sterilizing steam through sterilizing cabinet 300 and (2) prevents extraneous materials from passing through primary filter 306 and entering vent 304. Primary filter 306 is removable from sterilizing cabinet 300 and is typically replaced with a new filter following each sterilizing cycle.

Secondary filter 308 resides on top of primary filter 306 in filter holder 310. Secondary filter 308 covers primary filter 306 and forms a sealed interface with primary filter 306 in conjunction with filter holder 310 such that any sterilizing agent, such as sterilizing steam that passes through vent 304 must then pass through primary filter 306 and secondary filter 308. Secondary filter 308 can be made of any type of porous material that (1) allows for the passage of sterilizing steam from sterilizing cabinet 300 and primary filter 306 and (2) prevents extraneous materials from passing through secondary filter 308.

Exemplary embodiments of sterilizing cabinet 300 also include configurations wherein sterilizing cabinet 300 only includes a primary filter 306 and does not include the use of a secondary filter 308. Exemplary embodiments of this disclosure also provide for the embodiment that employs the use of a secondary filter 308 to form a sealed periphery with primary filter 306. In another exemplary embodiment the sealed interface between the primary filter 306 and the adjacent portion of either the sterilizing cabinet 300 is independent of an interface between secondary filter 308 and primary filter 306. In one exemplary embodiment, the primary filter 306 and the secondary filter 308 are coextensive.

In another exemplary embodiment, primary filter 306 and secondary filter 308 have different filter properties. For instance, primary filter 306 and secondary filter 308 may filter different elements of the sterilizing agent, which exits sterilizing cabinet 300 during a sterilization cycle. In an alternative exemplary embodiment, primary filter 306 and secondary filter 308 have similar filter properties. Another exemplary embodiment provides that primary filter 306 and secondary filter 308 are different colors.

Sterilizing cabinet 300 also includes legs 314, which reside on the bottom of sterilizing cabinet 300. Legs 314 provide spacing between the surface which sterilizing cabinet 300 rests and the bottom primary filter 306, secondary filter 308 and filter holder 310. In an alternative exemplary embodiment, legs 314 provide spacing between the surface which sterilizing cabinet 300 rests and the bottom primary filter 306 and filter holder 310. In this alternative embodiment, sterilizing cabinet 300 does not contain secondary filter 308. It should be appreciated that legs 314 as depicted in FIG. 3 are only exemplary embodiments of the possible configuration of legs 314. In other exemplary embodiments, legs 314 include wheels (not shown) that allow for sterilizing cabinet 300 to roll on a surface. In this embodiment, legs 314 with wheels can include a locking mechanism that can selectively prevent the wheels from rotating when not desired. In yet another exemplary embodiment, legs 314 can include a flat bottom that allows sterilizing cabinet 300 to slide along a surface.

In another exemplary embodiment, legs 314 include a locking or attachment mechanism that provides a means for affixing sterilizing cabinet 300 to the top of a case cart. Exemplary locking or attachment mechanisms include slots, locks, clamps, clasps, notches, grooves, ramps and the like that would allow sterilizing cabinet 300 to removeably affixed to a surface.

Also shown in FIG. 3 is filter holder 310 for maintaining primary filter 306 and secondary filter 308. In another exemplary embodiment, filter holder 310 only maintains primary filter 306. Exemplary embodiments of filter holder 310 include a hinge which allows portions of filter holder 310 to swing open about the hinge such that primary filter 306 and secondary filter 308 can be removed or placed independent of one another. In other words, filter holder 310 allows for secondary filter 308 to be released and removed from filter holder 310 while simultaneously maintaining primary filter's 306 seal with sterilizing cabinet 300 over vent 304.

Figure 4:
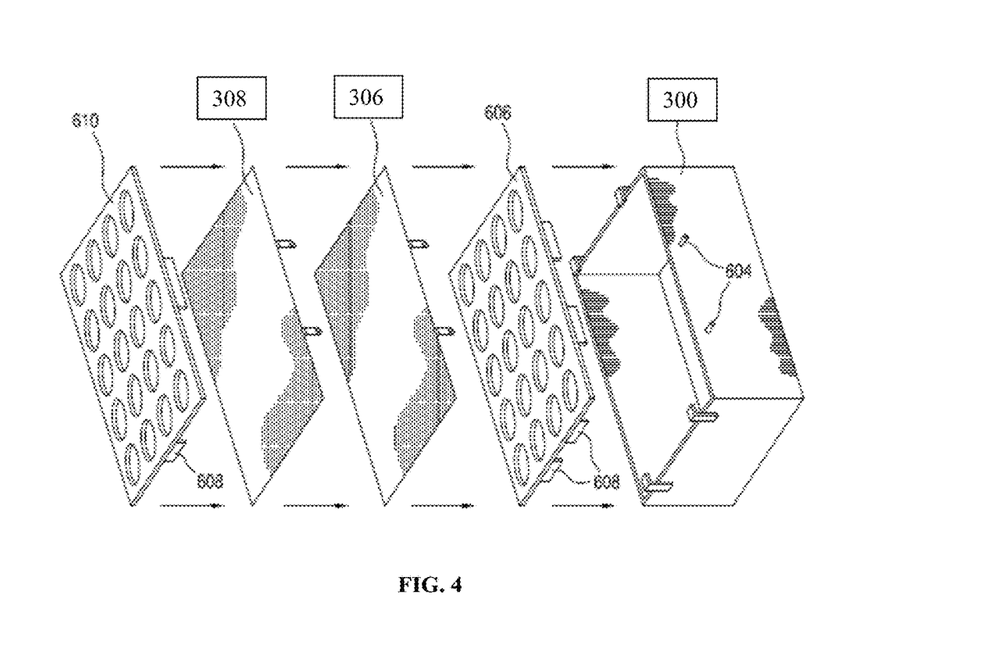
FIG. 4 is a perspective view of a filter arrangement suitable for use in practicing exemplary embodiments of this disclosure.

FIG. 4 is a perspective view of the construction of an alternative arrangement of sterilizing cabinet 300. As shown in FIG. 4, filter door 606 with clamps 608 attach around the frame of sterilizing cabinet 300. Primary filter 306 is placed on top of filter door 606 and attaches to sterilizing cabinet 300 at hooks 604. Secondary filter 308 is placed on top of primary filter 306 and also attaches to sterilizing cabinet 300 at hooks 604. Filter door 610 is then placed on top of secondary filter 308 and attached to sterilizing cabinet 300 with clamps 608. Exemplary embodiments of filter doors 606 and 610 include numerous holes or openings along their surface, which allow for the passage of sterilizing steam. In an alternative exemplary embodiment, secondary filter 308 is removed and only primary filter 306 is placed between filter doors 606 and 610.

Figure 5:
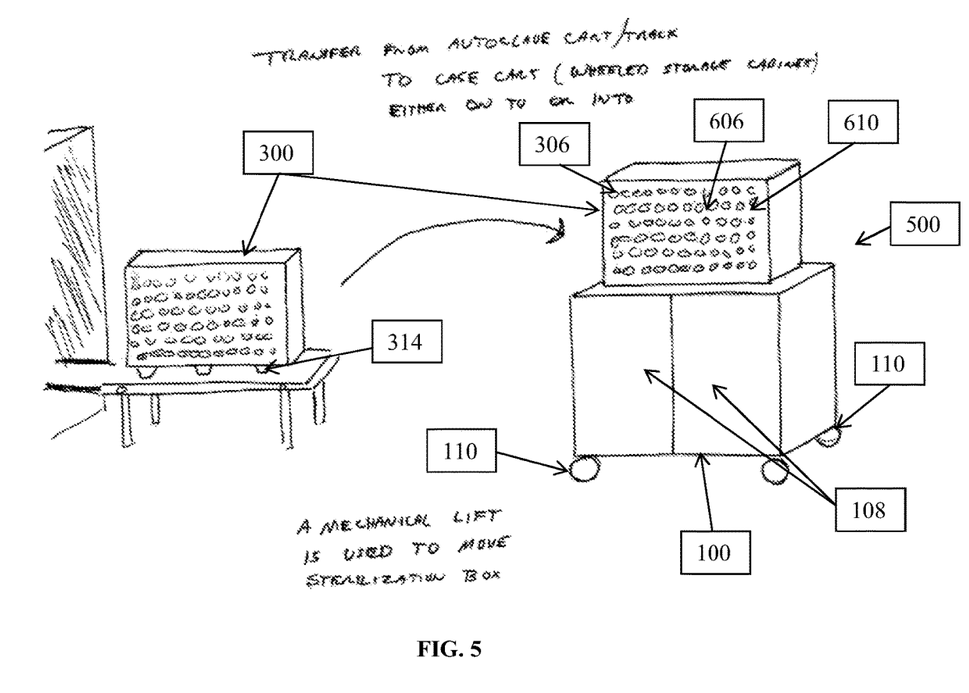
FIG. 5 is a perspective view of a device suitable for use in practicing exemplary embodiments of this disclosure.

FIG. 5 illustrates a device 500 suitable for practicing exemplary embodiments of this disclosure. Shown in FIG. 5, on the left hand side of the drawing is sterilizing cabinet 300 located on top of a stationary stand. After and during a sterilizing cycle, sterilizing cabinet 300 is typically located on or within a stationary object whether it be an autoclave or other similar device. Following the sterilizing cycle, as shown in FIG. 5, sterilizing cabinet 300 may be placed on top of case cart 100. Since sterilizing cabinet 300 may be quite heavy, depending on the contents of sterilizing cabinet 300, the use of a lift or mechanical lift can be employed to transfer sterilizing cabinet 300 onto case cart 100. Exemplary embodiments also include the use of a scissors lift, hydraulic lift, and pneumatic lifts that can be used to change the elevation of sterilizing cabinet 300 between the elevation at which sterilizing cabinet 300 is sterilized and the elevation at which sterilizing cabinet 300 is transported, such as the elevation of case cart 100.

As shown in FIG. 5, device 500 includes a sterilizing cabinet 300, which includes filter doors 606 and 610, primary filter 306. FIG. 5 also depicts device 500 as including a case cart 100, which includes doors 108 and wheels 110. It should be appreciated that sterilizing cabinet 300 and case cart 100 although not explicitly depicted in device 500 in FIG. 5 may include any of the elements previously described in this disclosure as it relates to sterilizing cabinet 300 and case cart 100.

In other exemplary embodiments, device 500 may include a processor, a memory including computer program instructions, a display, a controller, and a transmitter/receiver for tracking the contents of device 500. In this embodiment, the memory or non-transitory computer-readable memory including computer program instructions which when executed on the processor of device 500 can cause device 500 to track when each item enters or exits sterilizing cabinet 300 and case cart 100. This tracking system can be performed any type of unit tracking system, such as through the use of barcode scanners. The display will be able to communicate with the other elements of device 500 and display on demand the list of items within sterilizing cabinet 300 and case cart 100 and when a particular item was removed. Additionally, the transmitter/receiver will be able to communicate via wired or wireless networks the same inventory information shown on the display. The controller will be able to communicate with the other elements of device 500 and will allow a user to access the inventory of device 500.

Device 500 in FIG. 5 in practice maintains individually sterilized items in case cart 100 and collectively sterilized items in sterilizing cabinet 300. Device 500 thus provides a means to simultaneously access individually sterilized items as wells as collectively sterilized items.

Figure 6:
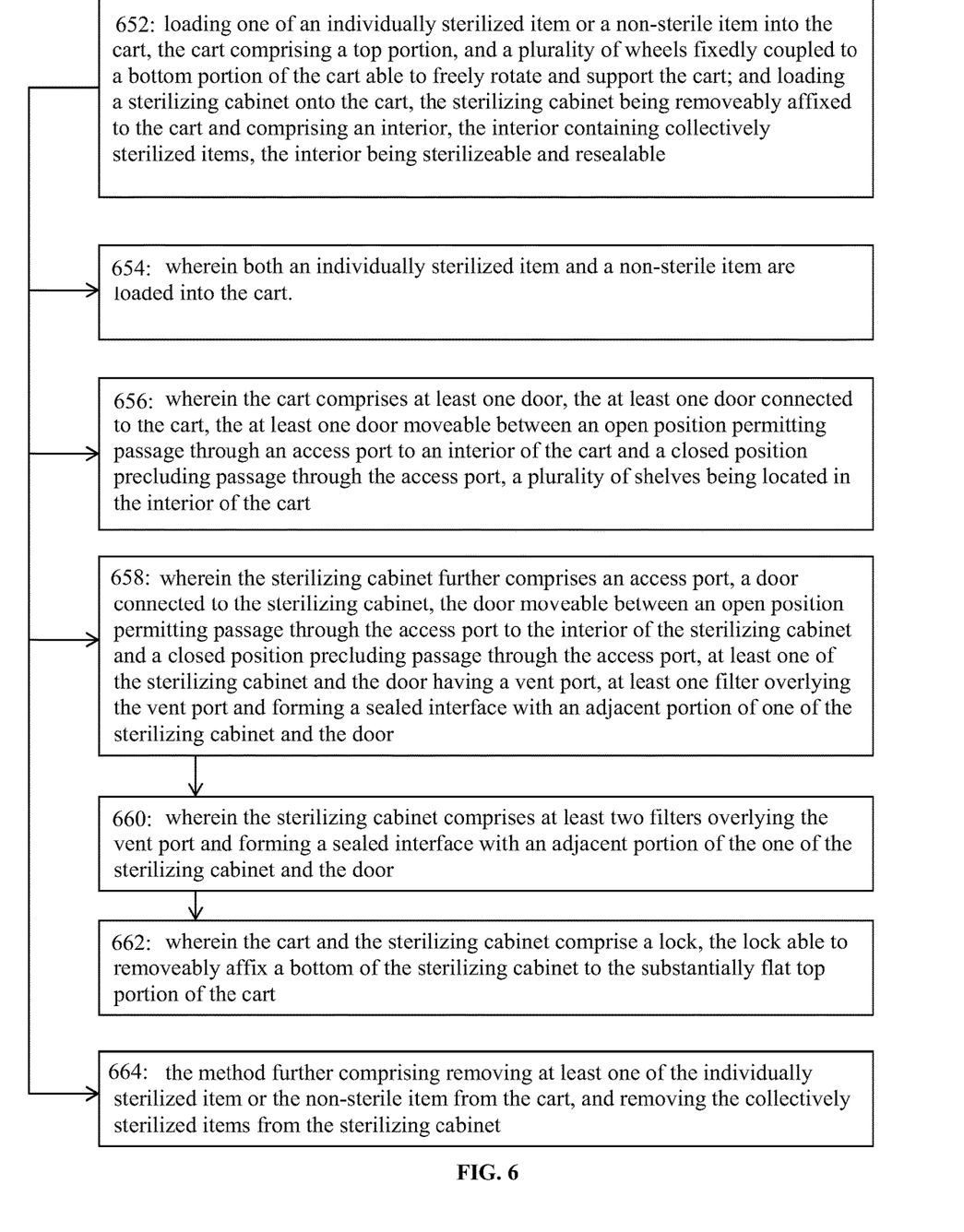
FIG. 6 is a logic flow diagram in accordance with a method and apparatus for performing exemplary embodiments of this disclosure.

FIG. 6 presents a summary of the above teachings for loading device 500 in the form of a logic diagram. The logic diagram of FIG. 6 may be considered to illustrate the operation of a method. Block 652 presents loading one of an individually sterilized item or a non-sterile item into the cart, the cart comprising a top portion, and a plurality of wheels fixedly coupled to a bottom portion of the cart able to freely rotate and support the cart; and loading a sterilizing cabinet onto the cart, the sterilizing cabinet being removeably affixed to the cart and comprising an interior, the interior containing collectively sterilized items, the interior being sterilizable and resealable. Then block 654 specifies wherein both an individually sterilized item and non-sterile item are loaded into the cart.

Some of the non-limiting implementations detailed above are also summarized at FIG. 6 following block 654. Block 656 relates to wherein the cart comprises at least one door, the at least one door connected to the cart, the at least one door moveable between an open position permitting passage through an access port to an interior of the cart and a closed position precluding passage through the access port, the plurality of shelves being located in the interior of the cart. Block 658 specifies wherein the sterilizing cabinet further comprises an access port, a door connected to the sterilizing cabinet, the door moveable between an open position permitting passage through the access port to the interior of the sterilizing cabinet and a closed position precluding passage through the access port, at least one of the sterilizing cabinet and the door having a vent port, at least one filter overlying the vent port and forming a sealed interface with an adjacent portion of one of the sterilizing cabinet and the door.

FIG. 6 at block 660 further specifies wherein the sterilizing cabinet comprises at least two filters overlying the vent port and forming a sealed interface with an adjacent portion of the one of the sterilizing cabinet and the door. Block 662 then specifies wherein the cart and the sterilizing cabinet comprise a lock, the lock able to removeably affix a bottom of the sterilizing cabinet to the substantially flat top portion of the cart. FIG. 6 then concludes at block 664 which specifies the method further comprising removing at least one of the individually sterilized item or the non-sterile item from the cart, and removing the collectively sterilized items from the sterilizing cabinet.

Thus, the present disclosure provides a method and apparatus for loading individually sterilized items into a device and loading a cabinet containing collectively sterilized items onto the device. This has the effect of providing a device that has the characteristic of being able to provide simultaneously accessible individually sterilized items and collectively sterilized items.

The invention claimed is:

1. A method of loading a sterilizable cart, the method comprising:
    (a) loading one of an individually sterilized item or a non-sterile item into the sterilizable cart, the sterilizable cart having an access port defined by (i) an integral top portion of the sterilizable cart configured to maintain the weight of a sterilizing cabinet, (ii) a right side, a left side, and a back side, (iii) a vent-free bottom portion having a plurality of wheels fixedly coupled to the vent-free bottom portion of the sterilizable cart able to freely rotate and support the sterilizable cart, and (iv) at least one door connected to the sterilizable cart, the at least one door moveable between an open position permitting passage through the access port to an interior of the sterilizable cart and a closed position precluding passage though the access port, wherein an internal volume is defined by the right side, the left side, the back side, the integral top portion, and the vent-free bottom portion, and wherein the integral top portion comprises a planar portion that is at least partially permanently affixed to an edge of the right side, an edge of the left side, and an edge of the back side, and wherein the sterilizable cart further comprises a plurality of shelves located in the interior of the sterilizable cart;
    (b) loading a sterilizing cabinet onto the integral top portion of the sterilizable cart, the sterilizing cabinet being removeably affixed to the integral top portion of the sterilizable cart and comprising an interior, the interior containing collectively sterilized items, the interior being sterilizable and resealable; and
    (c) loading another sterilizing cabinet on one of the plurality of shelves located in the interior of the sterilizable cart, wherein the one of the plurality of shelves located in the interior of the sterilizable cart includes a lock, and wherein the lock is able to removably affix a bottom of the another sterilizing cabinet to the one of the plurality of shelves located in the interior of the sterilizable cart.

2. The method according to claim 1, wherein both an individually sterilized item and a non-sterile item are loaded into the sterilizable cart.

3. The method according to claim 1, the method further comprising removing at least one of the individually sterilized item or the non-sterile item from the sterilizable cart, and removing the collectively sterilized items from the sterilizing cabinet.

4. The method according to claim 1, wherein the another sterilizing cabinet is removably affixed within the interior of the sterilizable cart.

5. The method according to claim 1, further comprising a step of sterilizing the sterilizable cart in a sterilizer.

6. The method according to claim 1, further comprising a step of spacing a bottom surface of the sterilizing cabinet from the integral top portion of the sterilizable cart.

7. The method according to claim 6, wherein the sterilizing cabinet further comprises legs, and wherein the legs are attached to the bottom surface of the sterilizing cabinet.

8. The method according to claim 7, wherein the legs include a locking mechanism to affix the sterilizing cabinet to the integral top portion of the sterilizable cart.

9. The method of claim 1, wherein an access port of the sterilizing cabinet is sized to receive a plurality of trays.

10. The method according to claim 1, wherein the sterilizing cabinet further comprises an access port, a first door connected to the sterilizing cabinet, the first door moveable between an open position permitting passage through the access port to the interior of the sterilizing cabinet and a closed position precluding passage through the access port, at least one of the sterilizing cabinet and the first door having a vent port, at least one filter overlying the vent port and forming a sealed interface with an adjacent portion of one of the sterilizing cabinet and the first door.

11. The method according to claim 10, wherein the sterilizing cabinet comprises at least two filters overlying the vent port and forming a sealed interface with an adjacent portion of the one of the sterilizing cabinet and the first door.

12. The method according to claim 11, wherein the integral top portion of the sterilizable cart includes a lock, the lock able to removeably affix a bottom of the sterilizing cabinet to the integral top portion of the sterilizable cart.

13. The method according to claim 10, wherein the sterilizing cabinet comprises a second door moveable between an open position permitting passage through the access port to the interior of the sterilizing cabinet and a closed position precluding passage through the access port.

* * * * *